(12) United States Patent
Hungerford et al.

(10) Patent No.: US 6,378,527 B1
(45) Date of Patent: Apr. 30, 2002

(54) CELL-CULTURE AND POLYMER CONSTRUCTS

(75) Inventors: David S. Hungerford, Cockeysville; Carmelita G. Frondoza, Woodstock; Afshin Sohrabi, Columbia; Alan H. Shikani, Ruxton, all of MD (US); Abraham J. Domb, Efrat (IL)

(73) Assignee: Chondros, Inc., Towson, MD (US)

( * ) Notice: Subject to any disclaimer, the term of this patent is extended or adjusted under 35 U.S.C. 154(b) by 0 days.

(21) Appl. No.: 09/275,319

(22) Filed: Mar. 24, 1999

Related U.S. Application Data
(60) Provisional application No. 60/104,842, filed on Oct. 20, 1998, and provisional application No. 60/081,016, filed on Apr. 8, 1998.

(51) Int. Cl.$^7$ .............................................. A61B 19/00
(52) U.S. Cl. ................. 128/898; 623/13.11; 623/13.17; 623/13.18
(58) Field of Search ....................... 623/13.11; 435/402; 128/898

(56) References Cited

U.S. PATENT DOCUMENTS

| | | | |
|---|---|---|---|
| 4,304,866 A | | 12/1981 | Green et al. |
| 4,994,388 A | | 2/1991 | Hillegas et al. |
| 5,041,138 A | * | 8/1991 | Vacanti et al. ................. 623/16 |
| 5,081,030 A | | 1/1992 | Civin |
| 5,100,799 A | | 3/1992 | Mundt |
| 5,326,357 A | | 7/1994 | Kandel |
| 5,786,217 A | * | 7/1998 | Tubo et al. ................. 435/402 |
| 6,027,744 A | * | 2/2000 | Vacanti et al. ............... 424/426 |

OTHER PUBLICATIONS

Sharma—Chemical Abstracts vol. 122 (1995) Abstract 122: 196593a.

Abe—Chemical Abstract vol. 122 (1995) Abstract 122: 54202y.

Draenert—Chemical Abstracts vol. 120 (1994) Abstract 120: 144253d.

Thompson—Chemical Abstracts vol. 124 (1996) Abstract 124: 299033p.

Yoshimura Chemical Abstract vol. 120 (1994) Abstract 120: 280358u.

Frondoza et al—Biomaterials vol. 17 (1996) pp. 879–888.

Frondoza et al one page article—43rd Annual Meeting, Orthopaedic Research Society, Feb. 9–13, 1997, San Francisco, California.

Frondoza et al one page article—Fifth World Biomaterials Congress May 29—Jun. 2, 1996, Toronto, Canada.

Frondoza et al one page article—45$^{th}$ Annual Meeting, Orthopaedic Research Society, Feb. 1–4, 1999, Anaheim, California.

"Microcarrier cell culture–principles & methods" Amersham Pharmacia Biotech pp 97–99 1981.*

* cited by examiner

Primary Examiner—Corrine McDermott
Assistant Examiner—Thomas Barrett

(57) ABSTRACT

Cells grown on a microcarrier are separated from the microcarrier by enzymatically digesting the microcarrier. More specifically, chondrocytes may be grown on dextran microcarrier beadlets and then the beadlets digested using dextranase to separate the chondrocytes from the carrier. Cells can also be grown on chitosan microcarriers to be used for implantation. In addition, cells can be grown on polysaccharide polymers to be used as implant devices. Various polymers serve as scaffolds for cells to be used for implantation. The polymers can be used for cell culture as well as for preparing scaffolds useful for tissue replacement such as cartilage tissue.

7 Claims, 4 Drawing Sheets

CELL-CULTURE AND POLYMER CONSTRUCTS

RELATED APPLICATIONS

This application is related to provisional applications Ser. No. 60/081,016 filed Apr. 8, 1998 and Ser. No. 60/104,842 filed Oct. 20, 1998.

FIELD OF THE INVENTION

The herein disclosed invention finds applicability in the field of cell culture, as well as in the field of tissue substitute for tissue replacement.

BACKGROUND

Attempts at replacing or rebuilding diseased or damaged structures in the human body go back to 3000 B.C. It was not until the middle of the 1900's, however, that the use of synthetic materials for rebuilding body structures met with widespread and reproducible success. Advances in material science and biomaterials and science have afforded much of the success. The need for new and better implants exists in every field of medicine in which disease or trauma can be treated surgically.

As technology advances continue to improve the state of the art, the standards for successful implants continue to improve including strength, biocompatibility and elasticity. The new research being conducted today on growth factors and controlled drug release tell of the day when implant material will be expected to promote healing, dissipate disease and stimulate tissue regeneration. New horizons for implants and implantable materials are being developed through the coordinated efforts of biomedical engineers and surgeons who are best positioned to appreciate the problems that patients are facing and that need to be addressed.

Tissue engineering has opened a new frontier in the development of implant materials for surgery. The surgical specialties which are more apt to deal with cartilage grafts substitutes and bone graft substitutes are the fields of orthopedics, otolaryngology-head and neck surgery and facial plastic reconstructive surgery. Cartilage and bone graft substitutes can be used as temporary scaffolds in which new cartilage and/or new bone may grow, encouraging tissue regeneration rather than inert tissue replacement. The regeneration of tissue in a controlled and predictable manner may be achieved with biodegradable implants, where the scaffold or template will degrade and be absorbed by the body, and the living cartilage or bone cells will remain. Implants such as these will eliminate the concerns about the long-term stability and safety of implant material currently used for tissue augmentation, and obviate the concern about long-term implant failure due to mismatch at the implant-tissue interface.

Articular cartilage is frequently damaged in the course of common activities. In addition, osteoarthritis leads to the initial focal wear of articular cartilage in many joints, particularly the hip and the knee. There are approximately 500,000 total hip and knee prostheses implanted in the United States every year and more than 1,000,000 arthroscopies of the knee. In the case of the replacements, the condition usually started with focal loss of articular cartilage. Under normal circumstances, articular cartilage, once damaged, does not heal. Current treatment methods consist mostly of alleviating symptoms through the use of activity modification (restrictions), weight-bearing protection (canes, crutches, walkers), analgesics and anti-inflammatory drugs. Recently, the FDA has approved autologous cell therapy. In this method, Chondrocytes are harvested arthroscopically, multiplied in tissue culture and implanted in the articular cartilage defect in the knee under a periosteal flap. The procedure costs $30,000. Alternative concepts are in development, but none are approved.

The inventors have developed a unique way of multiplying human chondrocytes so that they rapidly multiply and don't lose their phenotypic expression. They invest these cells in a scaffold that allows the interaction of the scaffold and the cells to reproduce the physical attributes of the cartilage the implant is intended to replace. No current therapy other than cadaver cartilage transplant offers this potential. Cadaver cartilage transplant is ineffective over the long term, is expensive and transplant material is not readily available. It must be emphasized that neither the cells nor the scaffold alone will work. In both instances, success is dependent on an uncontrolled response from the body in an uncontrolled environment. In the past, such response has been unpredictable and the development of such a response has required long periods of inactivity on the part of the patient. The approach provides a mature mechanically functional implant to the patient at the time of implantation, requiring only sufficient time for the implant to unite to the host (4–6 weeks).

Most of the patients undergoing arthroplasty for the knee started with a focal lesion of the a knee that would have been amenable to treatment with chondrocyte-implant. At least 50% of the patients undergoing arthroscopy of the knee have a focal articular cartilage lesion that is amenable to treatment with the chondroctye implant.

The ideal implant material for the future will be capable of forming a living bond to tissue, providing a scaffold or template to allow cells to grow and multiply and lay a matrix that will fill defects in the body and promote tissue healing. The field of this invention involves the use of polymer constructs as scaffolds or templates to allow the growth and multiplication of autologous cells in culture, including chondrocytes (cartilage cells), oesteocytes (bone cells) oesteoblasts, chondrogenic cells, pluripotential cells and mucosal cells for tissue replacement and/or coverage.

Chondrocytes are the sole cellular component of articular cartilage. They are sparsely distributed in the cartilaginous matrix and occupy less than 5% of the tissue volume. Chondrocytes produce and break down macromolecules that make up cartilage. These macromolecules consist primarily of a collagen type II network embedded with high-molecular-weight proteoglycans. By maintaining the integrity of articular cartilage, chondrocytes play a key role in the load-bearing function of the joint.

Several strategies have been explored to expand the number of chondrocytes ex vivo. Most of these attempts involve propagating cells in monolayer culture, which allows them to proliferate. However, chondrocytes propagated in monolayer culture lose their original characteristics by assuming a fibroblastoid morphology and shift from production of collagen type II to type I. They also change synthesis of high- to lower-molecular-weight proteoglycans.

Attempts to maintain the original phenotype in monolayer culture have had some success by seeding chondrocytes in high density. Despite these modifications in culture conditions, not all chondrocytes reverted to the spherical, collagen type II producing cells. Under culture conditions in which cells are restrained from spreading out as in monolayer culture, chondrocytes were inhibited from proliferating. These methods are not able to provide sufficient numbers of chondrocytes with unaltered phenotype needed for analysis. There is therefore a need for a culture system that would allow chondrocytes to proliferate, as well as maintain their original characteristics.

One culture system that has been shown to facilitate cell proliferation, as well as maintain synthesis of cellular products, is the microcarrier suspension culture. This culture system was based on the original 'bioreactor' design to grow bacteria in large quantities.

Microcarriers have been utilized in the prior art to grow anchorage-dependent mammalian cells in large quantities. Cells attached onto microcarriers are maintained in suspension spinner culture under controlled levels of pH, oxygen, nutrient supply and mechanical agitation. At an appropriate time the cells are harvested. Existing methods provide fairly simple procedures for obtaining secreted products from the spent culture. However, the ease of recovering high yields of viable and functional cells from microcarriers has been a problem. Several factors contribute to the problem of harvesting viable cells. These factors include the chemical composition of the microcarriers, the charge on the microcarrier surface and the method of cell harvesting. The most common method of cell harvesting used is by trypsinizaion, which may not completely retrieve cells from the microcarriers.

With all of this in mind, applicants have perfected means for cell culture, retrieval and methods for using the cells for tissue implants when used along with polymer constructs.

CELL-CULTURE PRIOR ART

U.S. Pat. No. 4,994,388 to Hillegas et al discloses a method for culturing and harvesting, anchorage-dependent cells employing insoluble microcarrier beads coated with collagen. The cells attach and grow on the collagen coated microcarrier. Once growth is complete, the collagen is digested off of the microcarrier, and the cultured cells are separated from the insoluble microcarrier. This patent also discloses that the patentees have, in contrast to using collagen coated beads, used beads made entirely of collagen and found these latter beads to support the growth of some cells very well, but that other cells did not proliferate well on collagen-only beads. The patentees also found in contrast to collagen coated beads that collagen-only beads present a slower attachment of cells to collagen. In addition, the patentees found that harvesting cells from collagen-only beads presented difficulties in separation of the cells from the media in that there was contamination of the cells by soluble fragments of collagen. While the patent discloses applicability of their invention to anchorage-dependant cells, the patent does not disclose any specific cell, nor are chondrocytes specifically disclosed. The disclosure of the patent to Hillegas et al has no specific embodiment of a process for carrying out separation of a specific cell from a specific substrate with a specific enzyme.

Mundt in U.S. Pat. No. 5,100,799 discloses a method for releasing cells from microcarriers using trypsin to release the cells. The composition of the microcarrier is not disclosed in this patent.

Kandel in U.S. Pat. No. 5,326,357 discloses cartilage tissue reconstituted on a substrate. The method of this patent involves reconstituting cartilage tissue in vitro from chondrocytes cultured on a substrate.

Green in U.S. Pat. No. 4,304,866 teaches a method for producing a transplantable sheet of living keratinous tissue by culturing keratinocytes in a culture vessel and subsequently enzymatically detaching a sheet of keratinous tissue employing an enzyme. These sheets of keratinous tissue are to be used for producing skin grafts.

Civin in U.S. Pat. No. 5,081,030 teaches the release of cells from an affinity matrix. The enzyme used by Civin can be an enzyme selected from the group consisting of carbohydrases, proteases and lipases. The carbohydrase is to be used for cell surface glycolipids and glycoproteins. Cell culture on a microcarrier beadlet is not disclosed in this patent.

OBJECTS OF THE INVENTION

An object of this invention is to efficiently propagate cells in vitro on the surface of microcarrier spheres or microcarrier beadlets.

A further object of this invention is to propagate cells on microcarriers to promote proliferation of the cells and also to continue the synthesis of cell by-products characteristic of the cells.

A most important object of this invention is to produce cells free of microcarriers without the need to physically separate the carrier from the cell.

A still further object is to be able to retrieve cells for testing or analysis.

A further important object of this invention is to produce viable cells by culture for further propagation in tissue culture.

An important object of this invention is to efficiently culture cells in vitro to be subsequently used in vivo.

A significant object of this invention is to prepare cells in culture to be used in animal or human transplantation.

A major object of this invention is to produce cells, which are useful for forming an implant device.

A main object of the invention is to prepare a polymer having medical applicability.

Another object of this invention is to prepare polymers useful for supporting the growth of cells or tissues.

An important object of this invention is to develop a polymer to be used for preparing scaffolds for cells.

An important object of this invention is to form polymer beads used as a substrate for culturing attached cells, as well as a substrate for preparing cell seeded scaffold implants.

FIGURES

CELL CULTURE AND ENZYME SEPARATION

Figure 1:
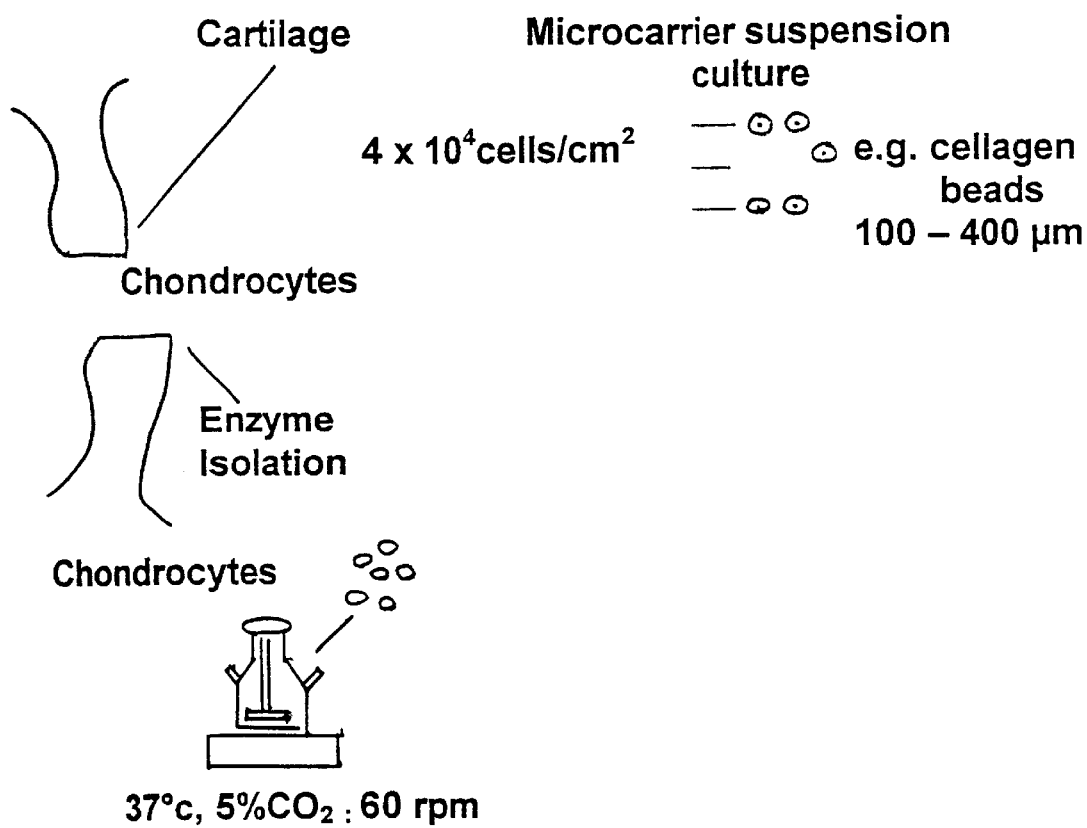
FIG. 1 is a schematic representation of the method of obtaining chondrocytes by culture on microcarriers, followed by enzyme isolation and then using the chondrocytes for cartilage repair.

The inventors have discovered a relationship between cell, substrate, enzyme and culture method.

Chondrocytes require special culture techniques in order to produce optimum growth, viability and maintenance of the cells in a non-altered form. Applicants' process involves primarily culturing chondrocytes along with dextran microcarrier beads and separating the cells from the microcarrier using dextranase.

The inventors have developed a procedure for successfully retrieving cells adhering to the surface of microcarriers. They employ enzymes, which completely digest the microspheres without damaging the cells. The paragraphs, which follow, describe (1) examples of cells that can be used, (2) types of microcarriers, (3) method of preparing the construct or microcarrier, (4) methods of culture, and (5) methods of harvesting the cells from the constructs.

The invention is directed primarily to the culture, harvesting and medical application of chondrocytes, oesteoblasts, oesteocytes, chondrogenic cells, pluripotential cells and mucosal cells.

The herein disclosed invention involves a rather defined process. The process involves allowing the cells to attach to microcarrier beadlets. The microcarrier beadlets are critical. The operative microcarrier beadlets require a special type of surface, as well as specific surface charge, to allow optimum cell adhesion and cell growth. In the herein disclosed invention, the terms microcarrier beadlets, beadlets or microcarrier are used interchangeably.

A most significant feature of the herein disclosed invention is the criticality between the microcarrier beadlet and the enzyme cleavage thereof. It is most important that the enzyme cleave the microcarrier beadlet in such a way as to not leave over sensible microfragments and debris. These microfragments and debris can have a deleterious affect on the cells, as well as causing cell-death. In addition, it is important that the enzyme used to digest the carrier not adversely affect the cell. The inventors have found that the combination of dextran microcarrier and dextranase as the 000 enzyme are ideal for growth and retrieval of chondrocytes.

For seeding, 1 ml of 1 to 2 $\times 10^5$ cells are added into 50 ml of media containing microcarries with a surface area equivalent to 400 $cm^2$ in a silliconized spinner flask with a 250 ml volume capacity. The mixture is intermittently stirred for 2 minutes every 30 minutes during the first 4 hours at 25 to 30 rpm. The cell microcarrier suspension is subsequently stirred at 45 rpm for another 4 hours. The speed is gradually increased to 60 rpm. The speed is maintained at 60 rpm for the desired duration of two weeks or longer. The final volume of the suspension culture is adjusted to 100 ml with warm medium. The final cell number is $2-3 \times 10^2/cm^2$. The spinner culture is replenished by sedimentation for 5 minutes. Approximately 50% of the volume is replaced every three days. The spinner cultures are incubated at 37° C., 5% $CO_2$.

To harvest the cells, the spinner microcarrier culture is sedimented. The supernatant is removed and the microcarriers are washed with Hank's buffered salt solution. The cells are retrieved by incubation with the dextranase enzyme at 7000 units 50/ml at 37° C. as shown in Table 3, page 6. To stop the enzyme reaction, 5 ml of medium is added and the supernatant fluid is discarded. The cell pellet is resuspended in 5 ml of tissue culture media for analysis.

The cells can be used for (1) direct implantation, (2) seeding on a scaffold, (3) reculture or (4) culturing to form a matrix.

The microcarriers of this invention must be generally smooth spheres. Particles with jagged edges are generally inoperative.

As used herein, the terms beads, microbeadlets, microcarriers and micropellets are used interchangeably, and they range in size from 1 to 300 microns.

Cells will be retrieved by non-toxic enzymatic digestion of microcarrier spheres while leaving cells viable and metabolically functional.

Chondrocytes are the only cellular constituent of articular cartilage. These cells are critically important in that they produce, as well as degrade, matrix components that make up cartilage. Understanding how these cells function has been facilitated by success in isolating viable chondrocytes and propagating them in vitro. Chondroctyes proliferate on a variety of tissue culture surfaces such as polystyrene and in resorbable biomaterials. Although chondrocytes cultured on these material divide, they shift to fibroblastoid cells and decrease their production of collagen type II and high molecular weight proteoglycans. We have previously demonstrated that chondroctyes, propagated on microcarriers made of solid collagen type I spheres, proliferate and maintain certain features of their chondrocyte phenotype. In the present study, we investigated whether dextran coated microcarriers coated with collagen type I can also be used to support the growth of chondrocytes and promote their synthesis of collagen type II. This collagen type serves as the matrix scaffold of articular cartilage. Identification of appropriate culture surface material will facilitate the propagation and analysis of chondroctyes.

Chondroctyes propaged on the surface of Cytodex 3® dextran microcarriers adhered tightly and could not be retrieved by trypsinization without damage. In contrast, cells recovered from Cellagen® microcarriers and monolayer cultures were viable. Cells on Cytodex 3® and Cellagen® microcarriers stained intensely for collagen type II. There was insignificant staining for type I. To further characterize de novo collagen synthesis radiolabeled collagens were analyzed. Chondrocytes on Cytodex 3® microcarriers synthesized and retained collagen type II in the cellular fraction (CF) more profoundly than cells propagated in Cellagen® microcarriers. In comparison, cells cultured as monolayer produced collagen type II which was more readily secreted out into the media fraction (MF).

It is important that the microcarrier beadlets not be toxic to the cells being cultured and equally important is the ability of the cells to adhere to the beadlets. The inventors have found that dextran microcarrier beadlets are particularly efficacious for culturing chondrocytes. The inventors have found that dextran microcarrier beadlets facilitate adhesion and growth of chondrocytes. The inventors have found that using dextranase the cells are readily separated from the dextran beadlets. Using dextranase to digest the dextran microcarrier beadlets, the inventors have found that dextranase is able to digest the dextran without producing fragments in the solution, thereby facilitating the separation of chondrocytes from the culture media.

The inventors have now found that the culture of chondrocytes on dextran microcarriers and digestion with dextranase to remove the carrier from the cell offers several unexpected and unobvious results. Applicants have found that chondrocytes grown on dextran microcarriers are able to adhere, be viable and produce extracellular matrix components such as collagen type II. In addition, separation of the cells from the dextran microcarriers with dextranase is efficient in that fragments of dextran do not interfere with efficient separation of the chondrocytes from the microbeadlets and do not adversely affect the viability of the chondrocytes.

The herein disclosed invention seeks to propagate cells in vitro on the surface of microcarrier spheres. The invention envisions the propagation of cells on microcarrier spheres that promote proliferation and continued synthesis of cell products characteristic of the cells being cultured. In the methods of this invention, cells can be easily retrieved for testing and analysis, as well as for further propagation and transplantation in animals and humans. The cells can also be plated onto a scaffold or matrix to be used for tissue replacement. In the processes of this invention, the cells after removal from the microcarrier beadlets will be viable and metabolically functional.

A variety of cells are amenable to the uses of this invention; however, chondrocytes, oesteoblasts, oesteocytes, monocytes, chondrogenic cells, pluripotential cells, mucosal cells and fibroblasts are most preferred.

Cartilage is composed of chondrocytes, which synthesize an abundant extracellular matrix, which is composed of water, collagens, proteoglycans and noncollagenous proteins and lipids. Collagen serves to trap proteoglycans and to provide tensile strength to the tissue. Type II collagen is the predominant collagen in cartilage tissue. The proteoglycans are composed of a variable number of glycosaminoglycan chains. The sulfated glycosaminoglycans are negatively charged resulting in an osmotic swelling pressure that draws in water.

It is most desirable that chondrocytes be maintained in a spherical shape which has been shown to slow down or prevent differentiation of the chondrocyte phenotype. Accordingly, it is important that culture systems be developed which maintain the spherical shape of the chondrocytes.

A wide variety of cells can be propagated on the surface of microcarrier spheres with the only requirement being that the cells adhere to the surface of the microcarrier sphere. Table I is a list of some of the cell types that can be successfully propagated on microcarriers.

TABLE I

LIST OF CELLS

1. Normal cells:
    a) Undifferentiated
        i] progenitor/mesenchymal cells — bone marrow cells, periosteal perichondral from the cambium
        ii] precursor cells, e.g. chondrogenic
    b) differentiated cells from:
        i] tissues — chondrocytes, osteoblasts, fibroblasts
        ii] peripheral blood — monocytes
2. Tumor cells — macrophage cell line, osteoblast cell line Cells originating from several species have been used for microcarrier culture. These include cells from rabbits, bovine, chickens and man.

Several types of microcarriers have tested and characterized in our laboratory as shown in Table II. These microcarriers were purchased from sources listed in Table II.

TABLE II

| Commercial Name | Commercial Source | Description | Size Diameter ($\mu$) |
|---|---|---|---|
| Cellagen | ICN | Collagen beads are prepared from bovine corium insoluble collagen by pepsin treatment. The collagen is then purified and formed into microsphere beads. | 100–400 |
| Cytodex 1 | Sigma | Cytodex 1 microcarriers are based on a cross-linked dextran matrix which is substituted with positively charged N,N-diethylaminoethyl (DEAE) groups to a degree which is optimal for cell growth. | 131–220++ |
| Cytodex 2 | Sigma | Cytodex 2 microcarriers are formed by substituting a cross-linked dextran matrix with only a surface layer of positively charged, N,N,N-trimethyl-2-hydroxy-aminopropyl groups. | 114–198++ |
| Cytodex 3 | Sigma | Cytodex 3 microcarriers consist of a surface layer of denatured collagen covalently bound to a matrix of cross-linked dextran. | 133–215++ |

++Diameter at 5% and 95% of the volume of a sample of microcarriers.

The method for preparing the cell microcarrier constructs are described as follows:
Preparation of Cellagen microcarriers
Cellagen microcarriers are purchased ready to use in sterile preparation.
Preparation of Cytodex microcarriers
for a surface area of 1000 cm$^2$, the following measurements are required for different Cytodex microcarriers:
1) Cytodex 1-6000 cm$^2$/g @ 1000 cm$^2$–0.1667 g
2) Cytodex 2-5500 cm$^2$/g @ 1000 cm$^2$–0.1818 g
3) Cytodex 3-4600 cm$^2$/g @ 1000 cm$^2$–0.2174 g
To a clean siliconized 250 ml spinner 50 ml of sterile 1×PBS is added followed by the addition of the desired Cytodex microcarrier. The cytodex carriers are allowed to rehydrate at room temperature overnight. The next day, the microcarriers are washed two times with sterile 1×PBS and are then ready to be autoclaved.

The microcarriers are seeded with cells according to the following procedures:
1. Cellagen microcarriers
   1. A 250 ml capacity spinner is cleaned, siliconized and autoclaved in advance. To the spinner is added 40 ml Hy(13) media: (Dulbecco's Modified Eagle Medium [DMEM], GIBCO-BRL); NCTC-109(GIBCO-BRL); oxaloacetate; pyruvate; insulin; L-gluatamine (GIBCO-BRL); gentamycin (BIOWHITAKER); fetal calf serum (Gemini Bioproducts, Inc.). Chondrocytes ($4\times10^6$ are next added to 3.95 ml=1000 cm$^2$ cellagen bead suspension.
   2. The spinner flask is placed on the stirring plate on the incubator @ 37 degrees, 5% $CO_2$, and the plate is set at interval mode (2 minutes on, 30 minutes off, 35 rpm). The spinner is incubated at these settings overnight.
   3. The stirring plate is switched to continuous mode after the cells have attached to beads. The stirring plate is set to 45 rpm in the morning. At the end of the day, the stirring plate is switched to 60 rpm continuous mode where it will stay for the remainder of the experiment, e.g. for about two weeks.
2. Cytodex I, II, III microcarriers
   1. A 250 ml spinner containing rehydrated cytodex microcarriers is autoclaved for 15 minutes on liquid mode. After autoclaving, the microcarriers are allowed to settle and cool off in a sterile hood. The 1×PBS is replaced with 40 ml of fresh HY media to spinner cells are finally added $4\times10^6$.

The seeded microcarriers are subsequently cultured at 37° C., 5% $CO_2$ for the duration required, e.g. for about two weeks. The schematic diagram of the procedure is shown in FIG. 1.

Cells are retrieved from microcarriers using enzymes selectively directed to digest the microcarrier without damaging cells. Table III shows the enzymes to be used for each specific microcarrier.

TABLE III

ENZYMATIC RETRIEVAL OF MICROCARRIERS

| Micro-carrier | Enzyme | Enzyme Commercial Source | Digestion Procedure |
|---|---|---|---|
| Cellagen | Collagenase | Collagenase A from Clostridium hystolyticum Supplier: Boehringer Mannheim | Incubate culture with .1% Collagenase for 1.5 hours |
| Cytodex 1 | Dextranase | Dextranase Source: Penicillium sp. Code: DEXC Supplier: Sigma | Incubate culture with 7000 units/ 50 ml for 1.5 hours |
| Cytodex 2 | Dextranase | Dextranase Source: Penicillium sp. Code: DEXC Supplier: Sigma | Incubate culture with 7000 units/ 50 ml for 1.5 hours |
| Cytodex 3 | Dextranase | Dextranase Source: Penicillium sp. Code: DEXC Supplier: Sigma | Incubate culture with 7000 units/ 50 ml for 1.5 hours |

The cell suspension isolated from the microcarriers are sieved through a 150 (100 µm) mesh collector (A. H. Thomas, PA, USA). The cells are pelleted by centrifugation at 200 g for 10 minutes. The supernatant fluid is discarded and the cells are resuspended in 5 ml of tissue culture fluid for analysis or for use in implantation.

The inventive process also involves separating the chondrocytes from the microcarrier beadlets, plating the chondroctyes on a scaffold or template for growth thereon and then surgically implanting the scaffold for cartilage repair.

In another embodiment of this invention after separating the cells from the microcarrier beadlets the cells can be injected into a patient in need of said cells.

Advantages of Invention and Improvements Compared to Existing Technology

The cell microcarrier constructs propagated in spinner suspension culture provide a twenty fold multiplication of cell numbers compared to monolayer cultures. The cells retrieved from the microcarriers remain viable, metabolically active and continue synthesis of "cell specific" products. In the case of chondrocytes, the "cell specific" products which characterize these cells are the cartilage matrix components-collagen type II and high molecular weight proteoglycans. Thus the cell numbers can be scaled up for mass production in bioreactors without compromising cellular function.

The constructs can easily be prepared and the cells removed for subsequent in vitro usage or for transplantation in animals or man in conjunction with a scaffold or template. Preparation of the cell-microcarrier construct is cost effective and requires less involved technical time and effort, as well as lesser amounts of tissue culture reagents as compared to preparation of monolayer cell cultures.

POLYSACCHARIDE POLYMER CONSTRUCTS

There is a continuing quest for developing ways for efficiently culturing cells and tissue. Cells are useful for producing cell by-products used in medicine, as well as in other fields. In addition, cells can be used for preparing products to replace poorly functioning or inoperative tissue or body parts. The herein disclosed invention envisions using polysaccharide polymers in cell culture and for preparing scaffolds or templates for tissue implants.

CHEMICAL PATHWAY FOR PREPARING POLYSACCHARIDE POLYMERS

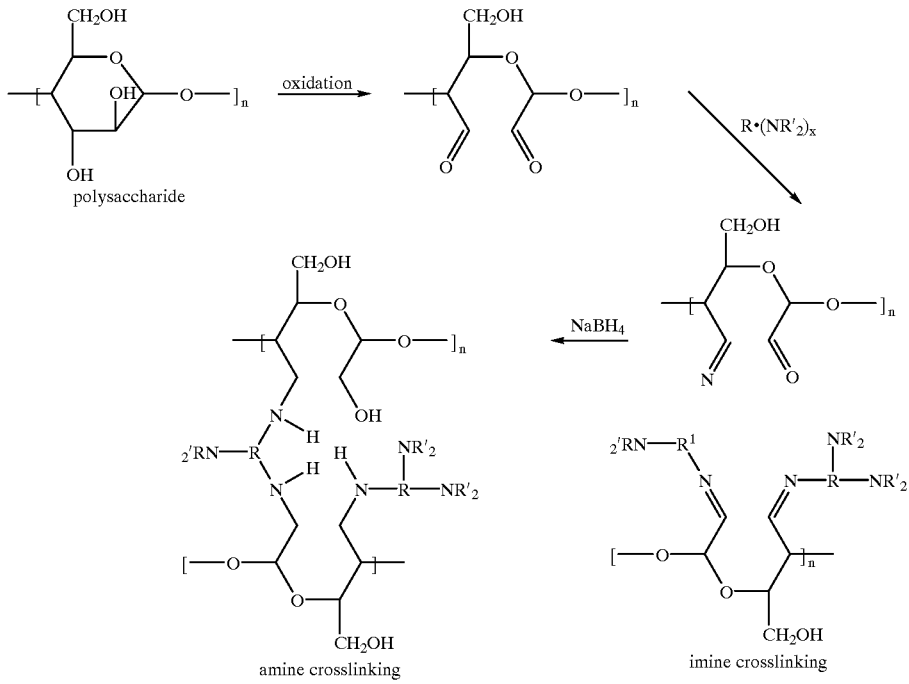

Polysaccharide include: dextran, cellulose, arabinogalactane
Oxidizing agents include: KIO4, NAIO4, ceric ammonium nitrate
R-(NR'$_2$)$_x$ is a polyanime coataining at least 2 primary amines. R' = H, alkyl
the catlonic groups in the crosslinked polymers include: 1⁰, 2⁰, 3⁰, 4⁰ amines In the complete structural formula of the polymer shown, there is imine and amine crosslinking, with the polysaccharide being linear or branched, natural or synthetic. Examples of polysaccharides useful for practicing this invention are dextran of various molecular weights, arabinogalactan, pollulan, cellulose and amylose obtained from various sources. The polyamine cationic and crosslinking agent contains at least two primary amino groups (for crosslinking) and primary, secondary, tertiary or quaternary amino groups. A single of mixture of polyamines can be used which include amino acides such as lysine and ornithine or peptides and proteins.

Polysaccharide includes: dextran, cellulose, arabinogalactan pollulan and amylose; n is an integer between 2 and 10,000 such as in a disaccharide, oligosaccharide or polysaccharide; oxidizing agents for oxidation include: $KIO_4$, $NaIO_4$, ceric ammonium nitrate; $R(NR_2)_x$ is a polyamine containing at least 2 primary amines; $R=H$, alkyl or alkylene; the cationic groups in the crosslinked polymers include: 1°, 2°, 3°, 4° amines, for example, these groups can be primary amine 1° ($R—NH_2$), secondary amine 2°

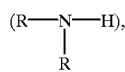

tertiary amine 30°

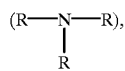

quaternary amine 4°

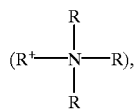

x can be between 2 and 5 (x determines the number of amine groups on the crosslinking molecule). For crosslinking it is essential to have a molecule that has at least two amine groups such as ethylene diamine.

The inventors envision the above chemical pathway for preparing the polysaccharide polymers. There is imine and amine crosslinking, with the polysaccharide being linear or branched, natural or synthetic. Examples of polysaccharides useful for practicing this invention are dextran of various molecular weights, arabinogalactan, pollulan, cellulose and amylose obtained from various sources. The polyamine cationic and crosslinking agent contains at least two primary amino groups (for crosslinking) and primary, secondary, tertiary or quaternary amino groups. A single of mixture of polyamines can be used which include amino acids such as lysine and ornithine or peptides and proteins.

The polysaccharide derived polymers with imine crosslinking, as well as amine crosslinking, can be used as microbeadlets for cell culture and the preparation of scaffolds for tissue repair.

In general, the specific method for making the polymer is as follows: The polysaccharides are first oxidized to the dialdehyde derivatives which is then reacted with non-toxic polyamines to form the imine crosslinking. The imine crosslinking bonds can be further hydrogenated to the more stable amine bonds.

The disclosed polymers of this invention are to be employed in the field of cell culture and. also for providing scaffolds useful for synthetic cartilage tissue formation. The disclosed invention also describes the synthesis of polysaccharide beads of different crosslinking densities, as well as the charge for facilitating the attachment and proliferation of cartilage cells on a polymer bead matrix. The cells (e.g., chondrocytes) will proliferate within and on the beads and form Collagen type II which is necessary for cartilage formation. When utilized in vivo, the beads will degrade to non-toxic components leaving chondrocytes in place to form cartilage tissue. The polymer beads are made of linear or branched polysaccharides crosslinked by diamino or polyamino molecules that are capable of forming an imine or amine bonds with the oxidized polysaccharide. The beads are prepared by reacting dialdehyde polysaccharides (prepared from the reaction of the polysaccharide with various amounts of potassium periodate at room temperature) with various amounts diamino molecules. The beads are designed to have a predetermined pore size formed by using different amounts of crosslinking and cationic groups that will enable optimum cell attachment. The polysaccharides that are useful for this method are biocompatible linear or branched polysaccharides and include among others: dextran, arabinogalactan, cellulose, pollulan and hyaluronic acid. The crosslinking agents are biocompatible diamine or polyamines exemplified by: lysine and ornithine, as well as their oligomers and polymers, such as gelatin or collagen. To enhance cell attachment to the beads, cationic sites are formed by adding a polycation such as polylysine, polyethyleneimine, gelatin, collagen, fibrin or albumin to the crosslinking reaction mixture. The imine conjugation bonds formed by the reaction of the amines with the aldehyde groups on the oxidized polysaccharides can be hydrogenated to form amino derivatives which contribute to the stability of the beads (i.e., amine groups are non-hydrolyzable in water solutions while the imines do hydrolyze) and in addition these imine conjugation bonds will also add a cationic charge to the beads. Anionic beads containing carboxylic acid groups can be formed by the addition of amino acids such as glutamic acid to the reaction mixture and, in this instance, the amino group will be conjugated to the polysaccharide and the carboxylic acid will be free.

Characteristics of the polymer: One of the main utilities of the polymer of this invention is to serve as scaffold for cell proliferation. The polymer should provide the proper environment for various cells to grow within and on the polymer beads. The characteristics and properties of the polymer should be versatile to allow the growth of various kinds of cells. For the various types of cells, the polymer should provide a hydrophilic micro environment of a specific pore size with cationic sites to allow for cell attachment. The degree of hydrophilicity, water absorption, pore size and cationic sites are similar for the cell types to be used in this invention but the polymer can be tuned to optimize the micro environment to each cell type by varying the chemistry. If the cells are seeded into the scaffold, the pore size of the polymer should be 50–100 $\mu$. The polymers should be insoluble in aqueous media but absorb water solutions to at least 30% of its weight. The polymer may swell to several times of its original volume without dissolution. The pore size of the swollen polymer gel should be in the range of 0.1 to 1 micron that can be controlled by the degree of crosslinking and the reaction conditions. The degree of crosslinking is dependent on the kind of polysaccharide, the degree of oxidation, the kind and amount of polyamine crosslinking agent and the method of preparation. The polymer should contain cationic groups to allow cell attachment. The concentration and kind of cationic groups, i.e., primary, secondary, tertiary or quaternary amines can be controlled. The gel may be degraded in an aqueous environment by chemical hydrolysis of the imine crosslinking bonds or by enzymatic degradation of the saccharide or peptide bonds.

The polymers should be biodegradable and resorb in vivo leaving cartilage cells and a matrix in place. Most importantly, the polymers should be compatible with cell-viability and allow cells to proliferate without toxicity or inhibition. In actual culture conditions, polymers of this invention have been found to be non-toxic to chondrocytes.

The herein disclosed polymers are intended to be used as microcarriers for cell culture; and particularly for the culture of chondrocytes. When the cells grow on the surface of the microcarrier, the size of the microcarrier should be 100–400 $\mu$. In addition, the polymers are intended to be used to form scaffolds on which chondrocytes are cultured and, in turn, used for cartilage replacement.

As used herein, the terms beads, microbeadlets, microcarriers and micropellets are used interchangeably, and they range in size from 1 to 400 microns.

PREFERRED EMBODIMENTS OF POLYSACCHARIDE POLYMERS CONSTRUCTS

EXAMPLES a: Cross linking of oxidized Arabinogalactan (AG)

Cross linking of oxidized AG was obtained from the reaction of oxidized AG (at least 20% of the sugar units are oxidized prepared by oxidation wit 0.1 molar $KIO_4$ in water on increasing mole ratio of saccharide to $KIO_4$) with 0.5 to 15% lysine. The gel-bead properties are dependent on the degree of oxidation of the polysaccharide, the content of the crosslinking agent, and the reaction conditions. The swelling capacity of the gel was determined by incubation of the crosslined polymer (100 mg) at room temperature over-night in 2.0 ml DDW (double-distilled water). The water-adsorbed gel was slightly dried by tissue paper and weighted, and then dried again by lyophilization to determine the content of insoluble gel. The % of water adsorption (calculated) was 210%.

b: Synthesis and characterization of poly-(carboxylic acid) gels based on di-aldehyde Arabinogalactan (AG).

In a typical experiment, different gels were prepared by the reaction of oxidized AG with L-glutamic acid and small quantities of lysine to introduce the cross linked gels. These gels were first reduced by sodium borohydride to introduce the stable amine cross-links (FIG. 1), and swelled for 24 hours in 37° C. in different pH media to calculate their ability to absorb water as a function of pH.

The pure oxidized AG (38% oxidation of saccharide units) was first dissolved in 0.1 M bicarbonate buffer pH=8.5 at a 10% $^w/_v$.

10% (w/v) and 25% (w/w) of L-glutamic acid powder were added. The corresponding amount of lysine (%) was added to the reaction mixtures and stirred for 24 hours in 37° C.

The different gels obtained were swelled over-night in a solution of excess sodium borohydride (1.5 mole excess over the aldehyde bonds) to reduce the imine conjugates to the more stable amine bonds, and to reduce the unreacted aldehydes units. The reduced-gels were washed several times with DDW to remove the excess borohydride and dried for 5 hours in a speed-vac system.

Synthesis of polycarboxylic hydrogels c: Albumin cross linking with oxidized Arabinogalactan (AG)

Albumin, a natural compatible protein containing amine groups, was reacted with increasing amounts of oxidized AG in order to obtain a cross linked gel. The experiment was as follows: 1.0 gr. of egg-albumin (or bovine serum albumin) was dissolved in 20.0 ml of 0.1M $NaHCO_3$ buffer and the solution was incubated for 15 minutes at 37° C. to obtain a clear-yellow solution which was then reacted with a solution of oxidized AG for 24 hours at 37° C. The molecular weight (MW), as well as the gel formation, were monitored. The results are summarized in Table 4. No significant change in MW was observed at a 10% (w/w) AG content, while at 0.5 to 1.0 weight ratio an insoluble gel was obtained. For comparison, a non-oxidized AG was reacted with albumin under the same conditions (Table 4, #6). No cross linking or interaction between the two polymers occurred as evident by the GPC data (two peaks for each polymer with the starting MW).

TABLE 4

Cross linking of albumin with oxidized AG

| | Egg Albumin mg/2.0 ml buffer | Oxidized AG (1:1) % W/W | MW |
|---|---|---|---|
| 1 | 100.0 | 0.0% | 332,341 |
| 2 | 100.0 | 1.0% | 379,332 |
| 3 | 100.0 | 10.0% | 472,562 |
| 4* | 100.0 | 50.0% | cross-linking |
| 5** | 100.0 | 100.0% | cross-linking |
| 6*** | 100.0 | 100.0 mg of the non-oxidized Arabinogalactan 372,332 (Albumin) 27,624 (Ox:AG) (two peaks) | |

*100.0 mg albumin reacted with 50.0 mg of oxidized AG(1:1). Gel water with 62% insoluble gel.
**100.0 mg albumin reacted with 100.0 mg of oxidized AG(1:1). Gel water with 77% insoluble gel.
***100.0 mg albumin reacted with 100.0 mg of non-oxidized chromatogram show two major peaks, one peak is relative to the non-oxidized AG.

The same procedure was employed using gelatin instead of albumin. A cross-linked gel was obtained at a 1:1 ratio. This gel absorb 256% of water with 87% insoluble gel. Cross-linking was detected also by using polyethyleneimine (PEI) with Ox:AG (1:1). No cross linking were detected by using oxidized Dextran instead of AG with all the proteins mentioned above.

d. Synthesis of beads based on crosslinked Arabinogalactan 1) 5% lysine Un-red (unreduced)

0.5 g of di-aldehyde Arabinogalactan (35% degree of oxidation) was dissolved in 4.5 ml DDW to give a 10% (w/w/) concentration of the polymer. 26.5 mg of lysine hydrochloride (5% weight to polymer) was added to the polymer solution and the pH was adjusted to 6.0 using 0.1M NaOH solution. Under these conditions crosslinking is very slow (pH=6.0). The mixture was added dropwise to an ice cooled decaline/buffer (0.1M NaHCO3, pH=8.0) two-phase system. While passing through the cold oil phase the droplets gel. At the alkaline pH of the water phase, reaction of lysine with di-aldehyde Arabinogalactan proceeds rapidly and the beads hardened. The beads are gently stirred in the buffer for 4 hour at 0° C. over-night at room temperature. Finally, the water-phase was separated from the oil-phase and lyophilized to dryness. The beads obtained were washed with DDW several times to remove soluble material, and then dispersed in ethanol at 4° C. overnight, filtered and dried in vacuum. The yield was =~90% by weight.

2) 5% lysine Red (Reduced)

Reduction of the Imine-bond obtained in 1) was done by incubating the beads in sodium borohydride solution (1.5 mol $NaBH_4$ for each mol sugar unit of polysaccharide) for 4 hours at room temperature, followed by filtration and washing with deionized water. The reduced beads were dispersed in ethanol at 4° C. over-night, filtered and dried in vacuum.

3) 20% lysine Un-red (unreduced)

These beads were synthesized exactly as 1) only using large amounts of lysine hydrochloride (125.0 mg. 20.0% weight).

4) 20% lysine Red (reduced)

Reduction of the Imine-bonds to the more stable amine bonds were done using the same procedure in 2). The crosslinked arabinogalactan beads identified as 5% lysine un-red (unreduced), 5% lysine Red (reduced), 20% lysine un-red (unreduced) and 20% lysine Red were tested and the results are described in FIG. 2. Bars 1–4 of the graph (FIG. 2) indicate that the particles tested did not have any toxic affect on bone cells. The proliferative capacity of bone cells exposed to the particles indicated by radiolabeled thymidine uptake is not statistically different from that of cells incubated in control medium alone (p<0.05).

5) AG-BSA 1:1

0.5 g di-aldehyde Arabinogalactan dissolved in 4.5 ml DDW were mixed with an equal volume of a 0.1M Borax-buffer (pH=6.0) containing 0.5 g Bovine-serum Albumin (BSA). The pH was maintained at 6.0 using 0.1M sodium hydroxide solution. The beads were added dropwise to a cold two phase system (decaline/pH=8.0 buffer) as described above. The beads obtained after lyophilization were dispersed in ethanol, filtered and dried in vacuum. yield =~90% by weight 6) AG-gelatin 1:1

These beads were synthesized as described in 5) only using Gelatin instead of Bovine-serum Albumin.

A crosslinked polysaccharide prepare by: 1) oxidation of a linear or branched polysaccharide to a dialdehyde derivative. 2) React the oxidized polysaccharide with molecule containing 2 or more reactive amino groups to form a crosslinked polymer with hydrolyzable imine bonds, or the crosslinked polysaccharide is further reduced to the amine linkages, such that the final product has a cationic charge to allow cell attachment The following is the chemical reaction and polymer produced which will be useful in carrying out the objects of this invention. For example, use in cell culture and for scaffolds used in transplant therapy.

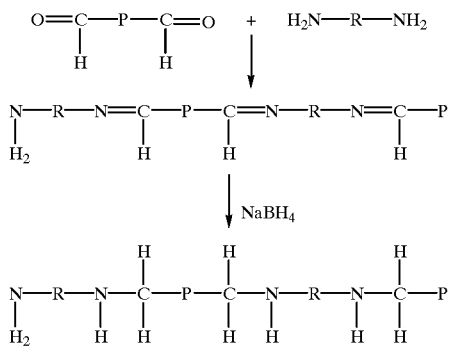

P is a polysaccharide such as: dextran, arabinogolactan, pollulan, cellulose, amylose—R is a residue of a molecule containing 2 amino groups or more such as: lysine, ethylenediamine, alkylenediamine, phenylenediamine, xylenediamine, polyethylenimine, gelatin, albumin, fibrinogen and

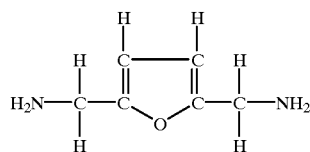

Preparation of Water Insoluble cationic Polymers for Controlled Charge of Polysaccharide Beads Three hydrophobized polyamines were prepared for use on polysaccharide beads. Polyethyleneimine (PEI) of 30,000 molecular weight (Polysciences, ratio of primary; secondary; tertiary amines was 1:2:1 respectively) was alkylated with stearyl bromide at a degree of alkylation ranged from 1 to 5% of the amine groups of the PEI. The reaction between dry PEI and stearyl bromide was carried out in a dry toluene at reflux for 5 hours. The solubility of the polymer in alcohol and in water was determined. Alkylated PEI containing 2 to 5% stearyl groups were insoluble in water but were soluble in alcohol. These PEI derivatives were applied on polysaccharide beads to increase cationic charge. Polylysine was hydrophobized to become insoluble in water by partial amidation (5 and 10% per amino groups) of the free amino side groups with stearic acid using dicyclohexyl carbodiimide (DCC) in dichloromethane at room temperature. The alkylated polylysine became insoluble in water but soluble in dimethylsulfoxide (DMSO). Preparation of acrylate based cationic polymers: To a polymerization kettle equipped with a stirrer and a nitrogen inlet it was added N,N-dimethylamino ethyl methacrylate (30 g), amino ethyl methacrylate (30 g), lauryl methacrylate (60 g), benzoyl peroxide (1.0 g) and dry toluene (300 ml). The kettle was immersed into a water bath at 70° C. and allowed to stir over night. After cooling to room temperature, diethyl ether (500 ml) as added and the white polymer precipitate was isolated by filtration and washed twice with diethyl ether and dried at room air. The polymer was soluble in dichloromethane but insoluble in water.

Coating of Polysaccharide Beads With Cationic Polymer

Crossliked arabinogalactan (AG) or dextran beads (0.5 g) were immersed in solutions of the hydrophobized polyamines in alcohol or dichloromethane (0.1 to 1% w/v, 5 ml) for 3 hours. The solvent was slowly evaporated to dryness using a vacuum evaporator at room temperature. The dry beads did not change their shape or average particle size after the addition of the polyamine. The amount of cationic charge was controlled by the concentration of the polyamine solution or by the amount of solution. The amount of amino groups on the beads was determined by nitrogen analysis.

Preparation of Micropellets

In general, an aqueous solution of the oxidized polysaccharide and polyamine at pH 6 (at this pH the crosslinking reaction is slow) is added dropwise to a buffer solution pH 8 (where fast crosslinking occurs) through a layer of decaline with stirring of the buffer solution. Spheres of particle size from 1 to 300 microns are formed in the high pH solution. The particle size and pore size are affected by the polysaccharide: polyamine ratio and concentration, the solution droplet size and stirring conditions. The droplet size can be controlled by using an automatic microinjunction device. Alternatively, a concentrated solution of the oxidized polysaccharide at pH 6.0 (5–20% w/v) is added dropwise with a rapid stirring into a solution of the polyamine at pH 8. Crosslinking occurred in a few minutes of stirring at room temperature. To add a cationic nature to the beads, a predetermined amount of a polyamine such as arginine, collagen, poly(ethylene imine) and its derivatives, poly(lysine), poly(ornithine), gelatin, fibronectin and laminine. Other charged or hydrophilic groups (carobxylates, amides and hydroxyls) can be added tot he polymer by adding the corresponding amino acids or amino containing molecules that contain the desired functional group.

PREPARATION OF SCAFFOLDING

The scaffolding. Cartilage cells or other cells are cultured within and on the beads by common methods as described in U.S. Pat. No. 5,326,357; Kandel et al, Biochem Biophys. Acta 1035:130, 1990. For example isolated chondrocytes are plated at a high cell density of between 1 and $10 \times 10^6/cm^2$ and placed in sterile tissue culture wells and cultured in fetal bovine serum medium at 37° C. in a $CO_2$ rich cell culture incubator. The crosslinked polysaccharide of this invention may replace the currently used coated agarose, cellulose, collagen or gelatin (Cultisphere) beads. Other uses of the polymer. The main use of these polymers is as scaffold for tissue regeneration, particularly cartilage. Beside chondrocytes, other cell types, e.g., for tissue engineering and regeneration can be prepared using these beads of this invention: hepatocytes, muscle cells, thyroid cells, langerhans cells, etc. Beads with a cationic nature can be used in chromatography for cell separation based on the bead pore size/cell size and the difference in the cell attachment to the cationic surface of the cell vis-a-vis, the anionic nature of the cell surface.

The crosslinked polysaccharide polymers of this invention are to be used for cell culture; and more specifically the crosslinked polysaccharide polymers can be formed into beadlets and chondroctyes, osteoblasts, monocytes and fibroblasts cultured thereon. It is expected that the cells can be digested off of the beadlets with an appropriate sugar digesting enzyme, e.g., amylase for amylose and dextranase for dextran. Moreover, the cells can be plated on a scaffold prepared from a crosslinked polysaccharide polymer.

Figure 2:
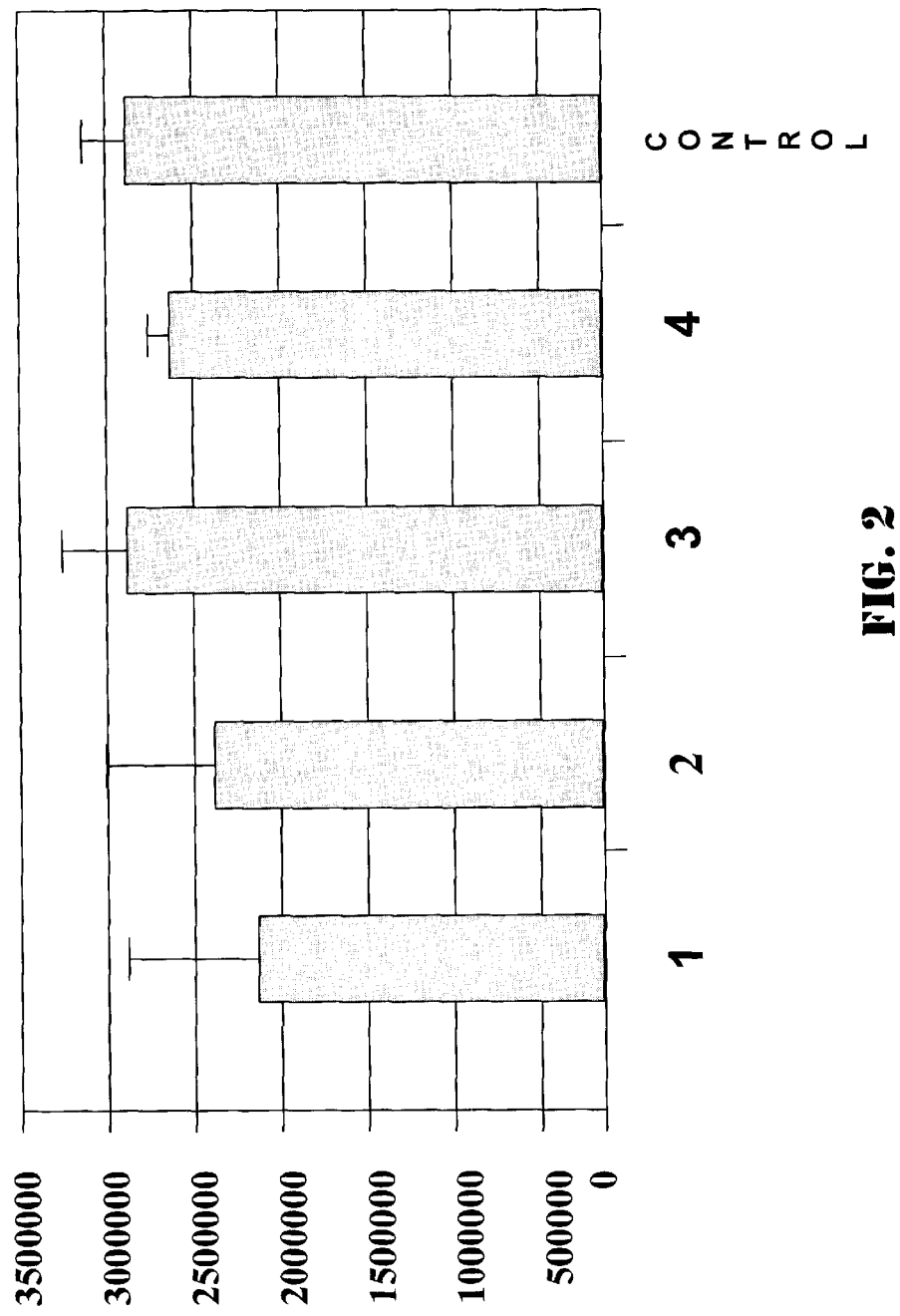
FIG. 2 is a graph describing the results of culture using arabinogalactan polysaccharide polymer particles on human osteoblast-like cells.

The chart of FIG. 2 shows the affect of the arabinogalactan polymer particles on human osteoblast-like cells.

While this invention focuses on tissue engineering of various cell types, it can be extended for the use of polymers in cell separation chromatography.

CHITOSAN CONSTRUCTS

Another elegant embodiment of this invention involves preparing a chitosan matrix containing cells for repair of cartilage or bone defects. Cells in the chitosan matrix are viable, metabolically active and continue to produce tissue specific products. The cell-chitosan constructs will be used to replace damaged or diseased cartilage.

Chitosan, a mucopolysaccharide is the alkaline deacetylated product of chitin, which is derived from the exoskeleton of crustaceans (1). The structure of chitosan shown in the enclosed figure is similar to glycosaminoglycans. It is crystallizable and can be prepared to yield a material with mechanical properties suitable for repairing cartilage defects (2–4). Biocompatibility studies in vitro and in vivo have indicated that chitosan is a non- cytotoxic, biodegradable material (5–7). With these physico-chemical properties, chitosan has been proposed for a variety of clinical applications. Chiosan as a biomaterial is currently being evaluated for use as a component of hemodialysis membranes, artificial skin, and in wound healing. The present invention is directed to a new application of chitosan to serve as cell scaffold for cartilage repair and particularly in articulating joints. The cells to be used for preparing the construct of this invention can be differentiated chondrocytes from cartilage or undifferentiated chondrogenic cells from the bone marrow, periosteum or perichondrium.

Articular cartilage is the resilient load bearing material critically important for normal joint function. This aneural and avascular tissue consists of a collagen type II flamework interspersed with aggregated proteoglycans called aggrecan (8–9), composed primarily of extracellular matrix and chondrocytes. Articular cartilage provides the excellent friction, lubrication and wear characteristics needed to meet the biomechical requirements in the joint. Chondrocytes comprise about 5% of the cartilaginous tissue but synthesize as well as degrade the extracellular matrix. The limited capacity of chondrocytes to proliferate and the lack of vascular supply underlie the inability of chondrocytes to repair itself when damaged as a consequence of mechanical trauma or disease. Superficial lesions that do not penetrate the subchondral bone do not heal adequately. Full thickness defects may heal but the repair tissue is made out of fibrocartilage (10). The fibrocartilaginous repair tissue does not have the physicochemical characteristics of the original hyaline cartilage thus compromising the biomechanical function of the joint(10).

Recent novel approaches for repair of cartilage include implantation of cells alone or cells seeded onto a scaffold (11–12). Whether cells are implanted alone or embedded in a delivery system such as a scaffold, they need to continue production of cartilage specific matrix components. A number of scaffolds have been proposed for cartilage repair (13–16). Actively metabolizing cells seeded on a scaffold have been shown to deposit their newly synthesized matrix components into the three dimensional framework simulating hyaline cartilage. Our proposed use of chitosan as a scaffold is conducive to producing viable and actively metabolizing chondrocytes or their precursors for producing cartilage extracellular matrix components such as collagen type II and aggrecan.

PREFERRED EMBODIMENT OF CHITOSAN CONSTRUCTS

We have discovered that human chondrocytes and other cells types such as osteoblastic cells can be successfully incorporated into chitosan constructs. The cells remain viable and are metabolically active indicated by their continued protein synthesis. They do not proliferate but continue to produce tissue specific matrix components. Chondrocytes produce collagen type II whereas osteoblasts produce collagen type I. The section below describes the (I) examples of cells that can be used in chitosan constructs, (2) types of chitosan tested in our laboratory, and (3) method of preparing the construct.

DESCRIPTION AND OPERATION

Differentiated chondrocytes or undifferentiated precursor cells from the bone marrow, periosteum and perichondrium can be incorporated into the chitosan scaffold described below. Several types of chitosan have been tested and characterized in our laboratory as shown in Table I Below. These chitosans were purchased from different sources.

TABLE IV

| Commercial Name | Commercial Source | Description |
| --- | --- | --- |
| Chitosan | Sigma | (Deacetylated chitin; Poly-[1-4]-[β-D-glucosamine) Practical Grade From Crab Shells Finesse: flakes may contain foreign matter |
| Chitosan | Seikagaku America | Code No. 400634; 83% Deacetylated Powder Crab Shell Finesse: 95% passed through 1000 μm |

TABLE IV-continued

| Commercial Name | Commercial Source | Description |
| --- | --- | --- |
| Chitosan | Seikagaku America | Code No. 400635<br>88% Deacetylated<br>Powder Crab Shell<br>Finesse: 95% passed through 1000 µm |

The method for preparing file encapsulation of cells in chitosan are described as follows:
1. Preparation of Chitosan
   a 2% solution of acetic acid is prepared
   for 3% & 6% (W/V) chitosan, the following measurements are required for all types of chitosan:
   a) For a 3 g solution—3 g of chitosan per 100 ml of acetic acid
   b) For a 6 g solution—6 g of chitosan per 100 ml of acetic acid To a clean 100 ml glass bottle 50 ml of 2% acetic acid is added followed by the addition of the desired chitosan concentration. The chitosan is allowed to dissolve at room temperature overnight. The next day, the chitosan is autoclaved. Once the chitosan is ready for use, cells are encapsulated according to the following procedures:
1. A sterile four well plate is put in the hood on advance. To one of the wells is added the desired amount of chitosan solution. Next, chondrocytes, in the pellet form ($\sim 4\times10^6$–$10\times10^6$), are added to the chitosan solution. A spatula is used to mix the chitosan-cell mixture. The mixture is stirred with file spatula until a ball is formed.
2. A 250-ml capacity beaker is cleaned and autoclaved in advance. To the beaker is added 50 ml of sterile filtered 1 N NaOH. Next, the chitosan-cell ball mixture is placed in the NaOH so that it polymerizes within minutes. After polymerization, the NaOH is quickly replaced with 50-ml of HBSS (GIBCO-BRL). The polymerized chitosan-cell ball is cultured in AIM V media (GIBCO-BRL) at 37° C., 5% $CO_2$ for the duration required.

Chondrocytes mixed with the chitosan becomes incorporated into a three dimensional structure as chitosan polymerizes within minutes after addition of NaOH. The cell-chitosan polymer has a firm consistency resembling the texture of cartilage. The incorporated cells appear viable as they continue to produce cartilage matrix extracellular components.

Advantages of Invention and Improvements Compared to Existing Technology

The cell-chitosan construct provides a biocompatible material to facilitate repair of cartilage defects. Chondrocytes or their precursors remain viable, metabolically active and continue synthesis of tissue-specific products. The chitosan scaffold or template serves as an ideal three dimensional environment for chondrocytes to maintain their production of cartilage specific collagen type II and high molecular weight proteoglycans. The constructs can easily be prepared for subsequent transplantation.

Chitosan is extremely promising because it has been used in other physiological applications and found to be compatible with body physiology. Because chitosan has been used in physiologic applications, FDA approval without undue delay is to be anticipated.

The invention envisions crosslinked polysaccharides with imine crosslinking and also amine crosslinking as exemplified in the chemical formulas set forth above to be used for cell growth attachment, as well as for the preparation of scaffolds for surgically implanting cells, such as chondrocytes for cartilage repair.

Viewed another way, the invention involves a scaffold or template for cartilage repair comprising a member of the group consisting of chitosan and a crosslinked polysaccharide prepared by crosslinking said polysaccharide with a polyamine, said member being shaped in the form of a scaffold or template and having plated and growing on said scaffold or template chondrocytes.

Another elegant embodiment of this invention involves the surgical implantation of the cartilage/bone polymeric scaffolds in the head and neck area. Tissue-engineered cartilage/bone using polymeric scaffolds and cartilage/bone cells can be used as an implant in plastic reconstructive surgery of the head and neck area. Studies in our laboratory have demonstrated the growth and multiplication of cartilage cells in vitro, with different types of polymers such as cellagen, arabinoglycan poysaccharide and chitosan, without toxicity to the cells. This opens possibilities for the production of viable and structurally stable cartilage in predicatable shapes originating from an autogenous cartilage, which in turn may be implanted for reconstructive or cosmetic purposes. The polymer-cartilage scaffold may be shaped into specific forms to fill defects in the head and neck area, or for the purpose of augmentation and facial sculpting.

Surgical applications and techniques for implantation of the polymer-cartilage scaffold include:
1) Nasal subcutaneous implantation for dorsal augmentation.
2) Thyroplasty for medialization of the vocal cord and treatment of vocal cord paralysis.
3) Subcutaneous implantation for facial reconstruction for congenital conditions (such as microtai, hypoplasia of mandible, of maxilla, of nose), and for acquired conditions (such as nasolabial fold augmentation, perioral augmentation, glabellar augmentation, premaxilla-nasal spine, malar complex, facial reanimation, facial defects from neoplasms, infection or trauma, defects of mandible, of maxilla, or nose, auricular reconstruction) and for cranioplasty.
4) Space augmentation via implantation or injection of the polymer-cartilage scafflod in order to improve function. For example, injection or implantation in the larynx or the vocal cord in order to improve vocalization, in the pharynx in order to improve swallowing, in the middle ear in order to provide support and improve hearing.

Besides being useful for cartilage repair in humans, the herein disclosed invention contemplates the use of scaffold or templates made of chitosan or a crosslinked polysaccharide prepared by crosslinking a polysaccharide with a polyamine. These scaffolds or templates have chondrocytes plated and growing thereon and are useful for cartilage repair in horses and particularly the cartilage of their knees.

In its most comprehensive form, this invention involves a surgical method for surgically implanting chondrocytes into cartilage tissue comprising the steps of:
1) Culturing chondrocytes on dextran microcarrier beadlets and thereafter separating the chondrocytes from the microcarrier beadlets by digestion with dextranse,
2) Plating and growing said separated chondrocytes on a scaffold or template manufactured from a crosslinked polysaccharide prepared by crosslinking said polysaccharide with a polyamine or alternatively plating and growing said separated chondroctyes on a scaffold or template comprising chitosan and then 3) Surgically implanting into cartilage tissue said scaffold or template having chondroctyes plated and grown thereon, to thereby repair cartilage tissue in a patient requiring cartilage repair.

A Surgical Technique for Cartilage Graft is set forth:

The following methodology applies to localized cartilage lesions suitable for laboratory grown autogenous cartilage grafts. The applicable lesion is excised down to subchondral bone using a #15 scalpel to create essentially vertical walls in intact articular cartilage. The walls should actually be cut so that the surface opening is slightly smaller than the lesion size at the level of the subchondral plate. This will create a three dimensional cavity which is slightly conical in nature with the top of the cone toward the articular surface. The base of the cavity is cleaned of all cartilage material, exposing but not penetrating the subchondral plate. Once the cavity is created, it is filled with cold-curing dental molding material that is allowed to set (~5 minutes). The mould of the lesion cavity is trimmed to the edges of the lesion and will serve as a template for cutting the graft implant to the exact size of the lesion. The walls of the graft are also trimmed to be slightly conical, with the top of the cone toward the surface that will become the articular surface. In this way the graft can be press fitted into the lesion and will be mechanically held in place by virtue of the precision fit and the conical shape of both the graft and the cavity into which it is to be placed.

Once the graft has been positioned in the site it must be tested for stability. If there is any question about the stability, ancillary stabilization can be created by suturing the edge of the graft to the lamina splendans of the periphery of the lesion with 5–0 interrupted sutures.

COMPREHENSIVE METHOD FOR SURGICAL CARTILAGE REPAIR

The herein disclosed invention finds applicability in the field of cell culture to produce viable cells and then using these cells for tissue repair in a patient. More specifically, the herein disclosed invention finds applicability in the field of cartilage repair. The invention contemplates the rapid and efficient obtaining of a sample of chondrocytes, comprising the steps of culturing the chondrocytes to obtain a sufficient sample of chondrocytes, preparing a chondrocyte containing scaffold and then surgically implanting the scaffold for cartilage repair.

Integrin And Collagen Expression Of Human Chondrocytes
Propagated In Microcarrier Spinner Culture
Introduction:

Cartilage turnover and metabolism depends on the interaction between chondrocytes and their surrounding extracellular matrix. Recent studies reported that the receptors on chondrocytes which mediate these interactions belong to the family of integrins (1). These proteins consist of heterodimeric, non-covalent complexes of alpha and beta subunits that act as transmembrane receptors which link the cytoskeleton and the extracellular matrix. The integrin mediated linkage, seems to play a critical role in the elaboration and maintenance of the extracellular matrix. We have previously discovered that human articular chondrocytes propagated on the surface of collagen microcarriers maintained in spinner culture actively produce collagen type II and proteoglycans which constitute the major extracellular matrix components of cartilage. (2). The mechanism by which the microcarrier spinner culture promotes expression of the chondrocytic phenotype has not been defined. The major objective of this study was to compare the relative expressions of integrin and collagen types I and II by human chondrocyte: a) immediately following surgical retrieval, and after two weeks of culture in b) monolayers or c) microcarrier spinners. We tested the hypothesis that the expression of integrin correlates with that of collagen type II. Integrins that act as binding sites for extracellular matrix components may help to maintain normal chondrocyte phenotype.

Methods:

Non-fibrillated articular cartilage was obtained from four osteoarthritic patients during knee surgery. Chondrocytes isolated by collagenase digestion were directly seeded onto Cellagen microcarriers (100–400 µm derived from bovine corium, ICN, Cleveland, Ohio) or as monolayer culture as previously described. Microcarrier and spinner cultures were incubated at 37° C., 5% $CO_2$ for fourteen days. Chondrocytes were harvested and the RNA was isolated by the TRIzol Reagent method (Life Technologies). A total cDNA library was synthesized using the Advantage RT-for-PCR Kit (Clonetech Laboratories, Palo Alto, Calif.) with oligo $(dT)_{18}$ primer. The resulting reverse transcriptase product was expanded using the SuperTaq Plus (Ambion, Austin, Tex.) PCR Kit and specific primers for collagen types I and II and integrin α5. This integrin chain sequence is of interest since it has been detected in articular cartilage. The housekeeping gene glyceraldehyde 3 phosphate (GPDH) was analyzed using the GPDH Control Amplimer Kit (Clonetech Laboratories). The PCR products were analyzed by electrophoresis in 1.5% agrose that contained ethidium bromide and photographed with UV light excitation. Production of integrins and collagens was verified by immunostaining using monospecific antibodies for α5 and for collagens with affinity purified antibodies to collagen types I and II (Fisher Scientific)

Results:

Integrin α5 and collagen type II were expressed in chondrocytes obtained directly from articular cartilage (P-0) or from monolayer (Mono) and spinner (Spin) cultures in all four cases examined as shown in a representative picture below. In contrast, collagen type I expression was not (2/2) or minimally (2/2) detectable at P-0 and in spinner cultures but was increased in monolayer cultures (4/4). The housekeeping gene GPDH was upregulated from P-0 to monolayer and spinner cultures indicating increased metabolic activity.

Discussion/Conclusion:

The principal finding of the present study is that the expression of integrin α5 parallels that of collagen type II in chondrocytes taken directly from articular cartilage and from monolayer or microcarrier spinner cultures. The observation that both genes are detectable at high levels suggests the potential for chondrocytes to readily synthesize the protein products. The observation that collagen type I expression is more prominent in monolayer cultures may indicate the progression into a fibroblastoid phenotype.

A feature of this invention encompasses the use of integrins, a glycoprotein, to serve as receptors to link chondrocytes. The inventors intend to use integrins to help facilitate the binding of chondrocytes to scaffold material, and particularly to bind chondrocytes to a chitosan matrix scaffold.

References:
1. Lapadula G., Iannone F., Zuccaro C., Grattagliano V., Covelli M., Patella V., Lo Bianco G., and Pipitone V. Clin and Exp Rhemnatol. 15:247–254, 1997.

2. Frondoza C., Sohrabi A., and Hungerford D. Biomaterials 17:879–888, 1996.

Chondrocyte Culture at Low Oxygen Levels

INTRODUCTION

Articular cartilage is an a vascular tissue and its oxygen supply is obtained by diffusion from synovial fluid or from the vasculature of the subchondral bone (1). It has been reported that the oxygen tension in cartilage is lower than other tissues. However, little is known as to the role of oxygen tension in the regulation of chondrocyte proliferation and phenotype expression. The present study tests the hypothesis that oxygen tension affects chondrocyte proliferation and function. Here we compare the response of human chondrocytes in monolayer and microcarrier spinner cultures to different oxygen tension in vitro.

METHODS

Chondrocytes were obtained from cartilage samples taken from an osteoarthritic patient at the time of total knee replacement. Cells were retrieved by collagenase digestion and seeded as monolayer or microcarrier spinner cultures as previously described (2). One set of monolayer and spinner flasks were incubated continuously from the time of seeding at either 5% or 20% (ambient) $O_2$. All cells were cultured at 37° C. with 5% $CO_2$. After 13 days of culture. samples of cells were pulsed with 8 $\mu$Ci/ml of $^3$H thymedine overnight. On day 14, the unlabeled cells were harvested for RNA isolation. The cells pulsed with $^3$H thymidine were cytocentrifuged onto microscope slides using Cytospin II (Shandon Lipshaw).

The RNA was isolated by the TRizol Reagent method (Life Technologies). A total cDNA library was synthesized using the Advantage RT-for-PCR Kit (Clontech Laboratories, Palo Alto, Calif.) with the oligo (dT) primer. The resulting reverse transcriptase product was expanded using the SuperTaq Plus (Amabion, Austin, Tex.) PCR Kit and specific primers for the sequences of interest. The housekeeping gene GAPDH was analyzed using the G3PDH Control Amplimer Kit (Clontech Laboratories). The PCR products were analyzed by electrophoresis in 1.5% agarose that contained ethidium bromide and photographed with UV light excitation.

The slides with $^3$H-thymidine labeled cells were dipped into NTB-2 emulsion (Kodak Imaging, Rochester, N.Y.) and incubated in the dark for 2 weeks at 4° C. They were developed with Dektol Developer and Fixer (Kodak) end counterstained with toluidine blue. The number of labeled and unlabeled cells were enumerated blind and the proliferative capacity expressed as percent labeling index. Statistical analysis was performed using the Jmp In statistical software (SAIS Institute).

RESULTS

Chondrocytes in microcarrier spinner culture incubated at 5% oxygen tension showed a lower proliferative index (p<0.0174) than at 20% oxygen tension. Monolayer cultures, which had a lower proliferative index than spinner cultures, were not affected by lower oxygen tension >0.05.

As shown in FIG. 2, RT-PCR of RNA from spinner cultures incubated at 5% oxygen showed a decreased expression of collagen type I RNA in the spinner cultures compared to those at 20% oxygen. In contrast, no change in collagen type I expression was noted in the monolayer cultures. Aggrecan RNA expression was also increased in the spinner cultures incubated in 5% oxygen but was unaffected in the monolayer cultures. In both spinner and monolayer cultures, the collagen type II RNA expression was increased at 5% oxygen cultures compared to 20% oxygen. The housekeeping gene GAPDH indicated equal loading for all samples.

DISCUSSION

The present study documents for the first time that low oxygen tension (5% $O_2$) similar to that of articular cartilage In vivo, inhibits chondrocyte proliferation while enhancing expression of the chondrocytic phenotype in microcarrier spinner culture. Our finding that chondrocyte microcarrier spinner cultures are more responsive to changes in oxygen tension than monolayer cultures supports our previous studies (2) that the former better simulates the physiological environment in the joint. Knowledge of the role of oxygen tension in regulating chondrocyte proliferation and gene function may help in propagating large numbers of functional chondrocytes for clinic applications.

A significant feature of the herein disclosed invention is the feature of culturing chondrocytes at a low oxygen tension when being seeded on to a scaffold. This feature is particularly useful when the chondrocytes are to be cultured onto a chitosan scaffold. The low level of oxygen is about 5% oxygen, however, amounts greater or less than 5% could be determined by those skilled in the art. It is expected that this low level of oxygen will enhance expression of collagen type II and aggrecan, as well as helping to maintain the chondrocyte phenotype.

REFERENCES:

1. Ysart, O E and Mason, R M. Biochemica et Biophysica Acta 1221:15–20, 1944.
2. Frondoza, C.; Sohrabi, A.; Hungerford, D.; Biomaterials 17:879–888 1996.

Figure 3:
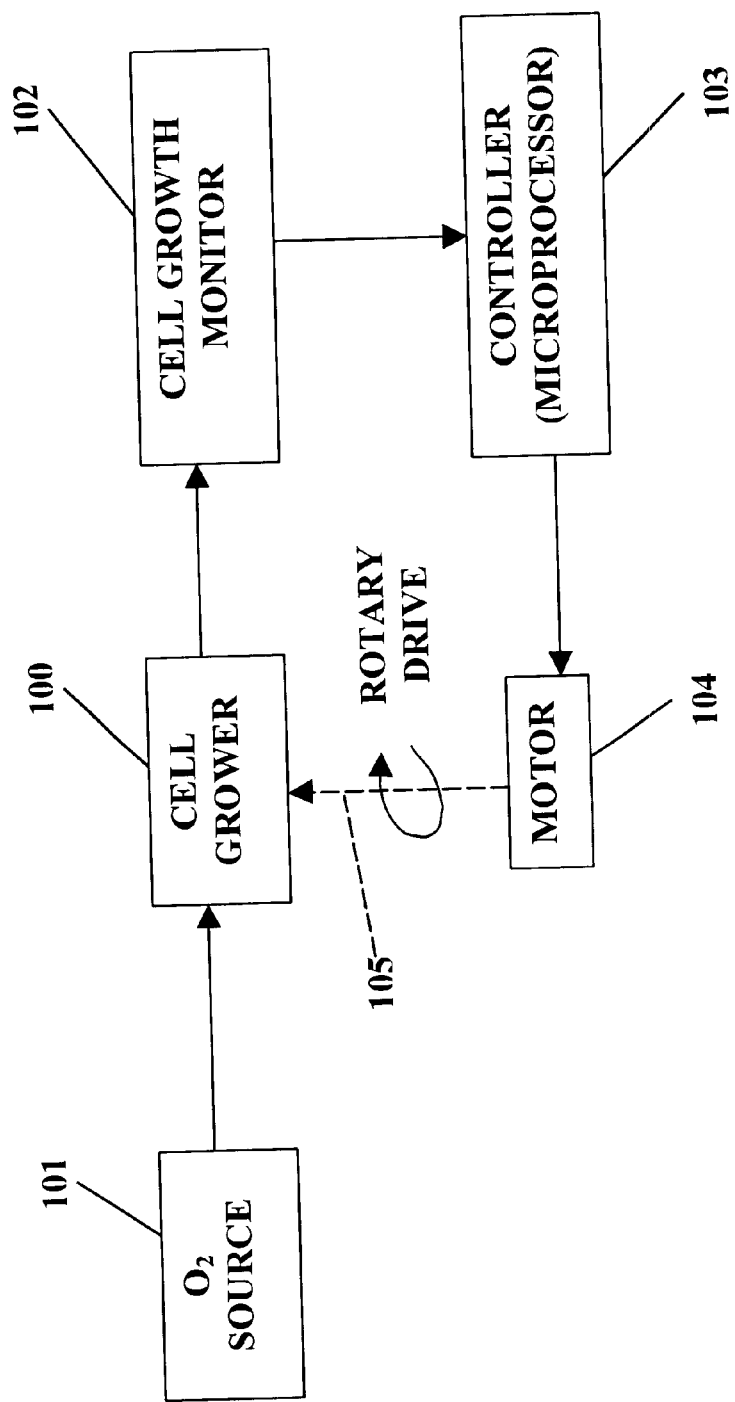
FIG. 3 is a schematic representation for the automatic control of conditions for cell culture.

An elegant embodiment of this invention involves a servo-mechanism or mechanism for the instantaneous adjustment of oxygen supplied to the chondrocyte cell culture in order for there to be optimum growth conditions for the chondrocytes in culture. This mechanism is described in FIG. 3 of the drawings. The mechanism has a oxygen ($O_2$) source 101 supplying oxygen to revolving culture chamber or cell grower 100 in which the culture takes place. This at times is referred to as a spinner culture. There is a cell growth monitor 102 which provides an output to controller (microrocessor) 103. The controller (microprocessor) 103, sends output to control motor 104 and rotary drive 105.

Chitosan Supports the Expression of Extracellular Matrix Proteins in Human Osteoblasts and Chondroctyes The need for biocompatible materials that can successfully support the growth and phenotypic expression of osteoblasts and chondrocytes is a major challenge in the tissue engineering of bone and cartilage. One candidate material that may fulfill this need is chitosan. Over the last twenty years, chitosan has been investigated for application in skin grafting, dental implantation, and drug delivery systems.[1-4] Chitosan is the deactylated product of chitin, a ubiquitous biopolymer found in the exoskeleton of marine invertebrates and the cell walls of fungi and yeast. Its unique properties include biocompatibility, bioactivity, and bioresorbability. Earlier reports described the utility of chitosan as a substrate for the growth of keratinocytes, fibroblasts, hepatocytes, and rabbit chondrocytes. However, little is known about the potential usefulness of chitosan in propagating human osteoblasts and chondrocytes. In the present study, we test the hypothesis that chitosan can support the proliferation and function of human osteoblasts and chondrocytes.

Methods and Materials

A 4% (w/v) solution of chitosan was sterilized by autoclaving and 100 $\mu$l was evenly pipetted into 24 well culture plates (Becton Dickinson, Lincoln Park, N.J.) fitted with 15 mm plastic coverslips (Nalge Nunc Intl., Naperville, Ill.). The chitosan films were then allowed to dry over a period of 24 hours. The acidity of the film was neutralized with a 0.5 N solution of NaOH. Excess base was then removed with repeat washings of Hanks Balanced Salt Solution. Plates were then sterilized under UV radiation for 48 hours. Normal human osteoblasts (Clonetics, Walkersville, Md.) maintained in monolayer cultures and condrocytes retrieved from two week old microcarrier spinner cultures were used for these experiments (5). Cells were seeded ($1 \times 10^5$/1 ml) into wells containing plastic coverslips coated with chitosan films. The same number of cells were seeded into control wells containing only ($1 \times 10^5$/1 ml) plastic coverslips. Cells were incubated over a period of 7 days at 37° and 5% $CO_2$. Cells propagated in the presence or absence of chitosan were retrieved by typsinization, cytocentrifuged, and immunostained for collagen type I, collagen type II, and keratan sulfate. Cell viability in situ was assessed using Live/Dead Assay (Molecular Probes, Eugene, Oreg.).

RNA was isolated from the remaining wells by the Trizol Reagent method (Life Technologies). A total cDNA library was synthesized using the Advantage RT-for-PCR Kit (Clontech Laboratories, Palo Alto, Calif.) with the oligo (dT) primer. The resulting reverse transcriptase product was expanded using the SuperTaq Plus (Ambion, Austin, Tex.) PCR Kit and specific primers for the sequences of interest. The housekeeping gene GAPDH was analyzed using the G3PDH Control Amplimer Kit (Clontech Laboratories). The PCR products were analyzed by electrophoresis in a 1.5% agarose gel that contained ethidium bromide and photographed with UV light excitation.

The search for biocompatible materials that can support the growth and phenotypic expression of osteoblasts and chondrocytes is a major challenge in the tissue engineering of bone and cartilage. Chitosan, a copolymer of glucosamine and N-acetylglucosamine, may provide a solution to this search. It is a deacetylated product of chitin, a ubiquitous biopolymer found in the exoskeleton of marine invertebrates and the cell walls of fungi and yeast. Little is known about its potential utility in propagating human osteoblasts and chondrocytes. Here, we tested the hypothesis that chitosan can promote the survival and function of osteoblasts and chondrocytes. Chitosan (4% w/v in 2% HAC) was prepared as: (1) film coatings or, (2) strand meshes. These were used for seeding human osteoblsts, MG-63 osteoblast-like cells or articular chondrocytes at $1 \times 10^5$/cells/well with or with chitosan film; or $2 \times 10^6$ cells/0.6 g of chitosan mesh. Cultures were incubated at 37°, 5% $CO_2$. RTPCR and immunocylochemistry were used to analyze the phenotype expression. Cell viability was assessed using a molecular probe vital dye.

Osteoblasts and chondrocytes appeared spherical and refractile on chitosan films whereas control cells ($\geq 90\%$) on plastic coverslips were elongated and spindle shaped through 7 days of culture. Greater than 90% of cells propagated in the presence or absence of chitosan remained viable. Human osteoblasts propagated on chitosan films continued to express collagen type 1, while chondrocytes express collagen type II and aggrecan. Osteoblastic cells cultured overnight on chitosan strands were adherent, remained viable and retained their spherical morphology.

The present work demonstrates the biocompatiibility of chitosan as a substrate for the growth and continued function of human osteoblasts and chondrocytes. The ability of chitosan to promote cell survival and extracellular matrix synthesis suggests its potential utility in tissue engineering.

Osteoblasts and chondrocytes plated on chitosan films appeared spherical and refractile when viewed by phase contrast microscopy after 24 hours of culture. In contrast, cells grown on plastic coverslips were elongated and spindle shaped. This difference was most striking in 3-day old control cultures where the majority of cells displayed a fibroblastic appearance. In comparison, less than 10% of cells grown on chitosan appeared fibroblastic. These differences persisted through the 7-day time point. Greater than 90% of human osteoblasts and chondrocytes propagated in the presence or absence of chitosan stained green indicating viability based on the vital dye assay. Less than 10% stained red, indicating insignificant toxicity after 7 days of culture. Human osteoblasts propagated in chitosan continued to express collagen type I. Similarly, human chondrocytes grown on chitosan film expressed matrix proteins, collagen type II and aggrecan. The ability of the cells propagated on chitosan to continue synthesis of extracellular matrix proteins, indicated by mRNA expression, was further confirmed by immunolocalization of the collagens and keratan sulfate. Osteoblasts propagated on chitosan stained intensely for collagen type I. Chondrocytes grown on chitosan, did not show significant staining for collagen type I, but stained intensely for collagen type II and keratan sulfate.

Of significance is the fact that osteoblasts and chondrocytes propagated on chitosan survive and continue expression of phenotype markers. Once the scaffolds are seeded with osteoblasts or chondrocytes, these seeded scaffolds can be used for repairing bone or cartilage defects.

In experiments a 4% (w/v) solution of chitosan was sterilized and pipetted into well culture plates and allowed to dry to form a film. The acidity of the film was neutralized and excess base was washed away with Hanko Balanced Salt Solution. Osteoblasts and chondrocytes were seeded ($1 \times 10^5$/ml) onto the chitosan film. After incubation for 7 days at 37° and 5% $CO_2$ and cell viability was assessed. Osteoblasts and chondrocytes plated on chitosan film appeared sperical and refractile after 24 hours of culture, while the same cells grown on cover slips were elongated and spindle shaped. Cells cultivated on chitosan continued their synthesis of extracellular matrix proteins.

In the herein disclosed invention, a preferred scaffold is one made of sponge chitosan.

References

1. Chandy, T. et al. Biomat, Art Cells. Art Org 18(1):1–24 (1990)
2. Denuziere, A el al., Biomaterials 19(1):1275–85 (1998)
3. Yagi, K el al., Biol Pharm Bull 20(12): 1290–4 (1997)
4. Koyano, T. J Biomed Mater Res 39:486–90 (1998)
5. Frondoza. C el al., Biomaterials 17:879–88 (1996)

Aside from being available from the knee, chondrocytes can be obtained from nasal septal cartilage and ear cartilage and/or costo-chondral cartilage. These cartilage sources of chondrocyte cells may be more readily available and easier to conveniently obtain.

Comprehensive Method of Use

Figure 4:
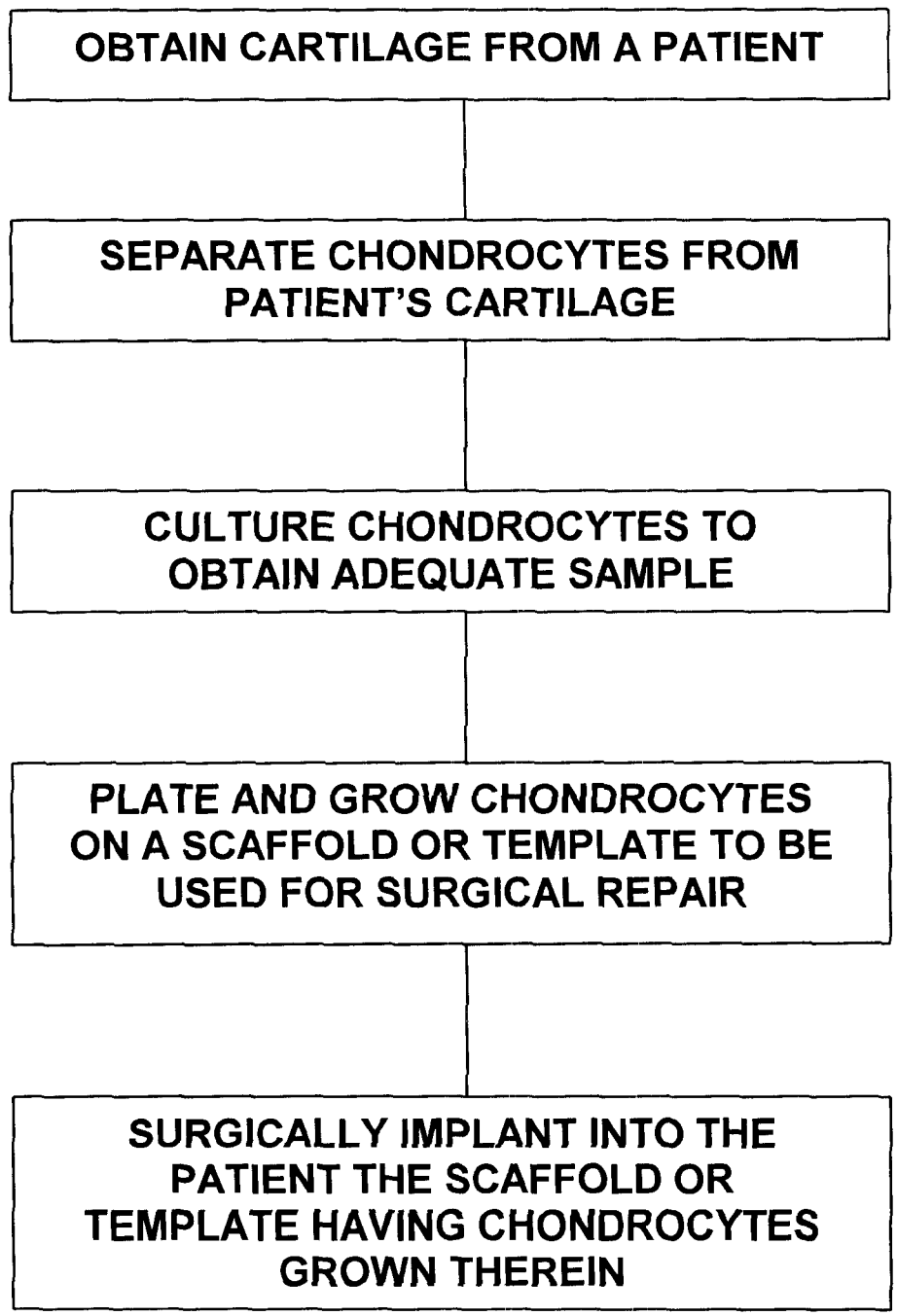
FIG. 4 is a flow chart describing rapid retrieval of chondrocytes and repair of cartilage.

The comprehensive method of this invention contemplates an efficient procedure for cartilage repair as shown in the flow chart of FIG. 4. The inventors contemplate cartilage repair in a patient wherein a small sample of cartilage is removed from the patient. Chondrocytes are separated from the cartilage tissue. These chondrocytes are then cultured to produce adequate numbers for seeding on a scaffold. Once seeding is complete, the scaffold with chondrocytes viable thereon is surgically implanted into the patient. The procedure disclosed herein contemplates a quick turn-around between the time of obtaining the patient-sample of cartilage and surgically implanting the chondrocyte-containing scaffold.

In its most comprehensive method, this invention involves:

Retrieval and Isolation of Chondrocytes From Cartilage

1. Cartilage will be obtained from the knee, nasal septal cartilage, ear cartilage and/or costo-chondral cartilage.
2. Cartilage tissue will be minced into small pieces in a plastic petri dish under sterile condition in the laminar flow hood.
3. The minced tissue will be placed in a culture jar containing 1 ml of 0.1% collagenae in HY:DMEM (1:1) medium.
4. The minced tissue will be incubated for 18 hours in an incubator at 37° C., 5% $CO_2$ to digest the matrix and separate chondrocytes.
5. The digested tissue and cell suspension will be passed through the Cellector screen (screen filter) to separate cells from undigested material.
6. The separated cell suspension will be centrifuged at 1000 rpm. The supernatant fluid will be pipetted out and then discarded. The cell pellet will be washed by resuspending in Hanks' balanced salt solution followed by centrifugation at 1000 rpm. The wash fluid will be pipetted out and then discarded. The cells will finally be resuspended in HY media and then counted for subsequent use or cryo-preserved for storage in liquid nitrogen.

Cell Culture

The cells obtained from tissue will be propaged on microcarriers and retrieved therefrom for use.

Preparation of the Cell-Seeded Scaffold or Contstuct

1. The material will be fashioned into a porous three dimensional sponge and scaffold. And more particularly, the fashioned material will be chitosan.
2. The shape, thickness and size for cell seeding will be configured to fit into the defect to be filled.
3. The cells will be seeded into the scaffold by applying the cell suspension on the surface of the scaffold such that the entire volume will penetrate through the scaffold.

Surgical Repair of Articular Cartilage
1. The cartilage defect will be prepared for transplantation of the cell-seeded construct or scaffold.
   A) The defect will be debrided and the area will be cleaned by saline irrigation.
   B) The defect may be treated with material (e.g. transglutamase) that could help glue and keep the construct in place.
2. A chondrocyte scaffold having been previously prepared will then be implanted into the prepared defect. The construct will be fitted into the defect to the level of the surrounding normal articular cartilage and then left as is.

ADVANTAGES OF THE INVENTION

The herein disclosed invention seeks to perfect cartilage repair surgery. The invention envisions overcoming many of the failings practiced by the medical profession and, particularly, the commercial practice of cartilage repair. The invention seeks to improve cartilage repair surgery in the following ways:

1) The invention will make available sufficient quantities of compatible chondrocytes required for repair (and in a relatively short period of time) by growing or culturing the chondrocytes in a spinning culture chamber and, preferably, at reduced oxygen levels.
2) The patient's own chondrocytes will be used to culture cells for plating onto the scaffold. Cadaver cells will not have to be used.
3) The invention envisions rapidly growing chondrocytes in culture.
4) Chondrocytes cultured will be characterized as having an approximately normal phenotype.
5) Scaffolds prepared for transplant will be physiologically compatible and resorbable into the body.
6) Cell culture and surgical facilities will be at a single location which will assure rapid and efficient surgical procedures envisioning a high surgical success rate. This should be contrasted with the correct medical procedures, which may be outlined as follows:

Taking chondrocytes from the patient for subsequent growing in a chamber (non-spinning and at ordinary oxygen levels) which reuires a relatively long time period to grow sufficient quantities of the chondrocytes for subsequent transplanting into the patient.

Taking chondrocytes from a cadaver, growing the chondrocytes and plating on a scaffold (or other plastic or inorganic support) and thereafter transplanting into the patient.

Obviously, many modifications may be made without departing from the basic spirit of the present invention. Accordingly, it will be appreciated by those skilled in the art that within the scope of the appended claims, the invention may be practiced other than has been specifically described herein.

REFERENCES

1. Tomihata, Kenji and Ikada, Yoshito: In vitro and in vivo degradation of films of chitin and its deacetylated derivatives. *Biomaterials* 18: 567–575, 1997.
2. Amiji, Mansoor M.: Surface modification of chitosan membranes by complexation-interpenetration of anionic polysaccharides for improved blood compatibility in hemodialysis. *J. Biomater. Sci. Polymer Edn*, 8: 281–298, 1996.
3. Austin, P. R.; Brine, C. J.; Castle, J. E.; and Zikakis, J. P.: Chitin: new facets of research. *Science* 212: 749–753, 1981.
4. Vasudev, Sindhu C.; Chandy, Thomas; and Sharma, Chandra P.: Development of chitosan/polyethylene vinyl acetate co-matrix: controlled release of aspirin-heparin for preventing cardiovascular thrombosis. *Biomaterials* 18: 75–381, 1997.
5. Taxavel, M. N. and Domard, A.: Collagen and its interaction with chitosan. *Biomaterials* 16: 865–871, 1995.
6. Maruyama, Masaaki and Ito, Michio: In vitro properties of a chitosan-bonded self-hardening paste with hydroxyapatite granules. *Journal of Biomedical Materials Research*, 32: 527–532, 1996.
7. Wan, Andrew C. A.; Khor, Eugene; and Hastings, Garth W.: Hydroxyapafite modified chitin as potential hard tissue substitute material. *J Biomed Mater Res* 38:235–241, 1997.
8. Kuettner, K. E.: Biochemistry of articular cartilage in health and disease. *Clin. Biochem.* 25: 155, 1992.
9. Mankin, H. J.: The reaction ofarticular cartilage to injury and osteoarthritis. *New Engl. d. Med.* 291: 1285, 1974.
10. Mankin, H. J. and Lippiello, L.: Biochemical and metabolic abnormalities in articular cartilage from osteoarthritic human hips. *J. Bone Joint Surg.* 52(3, Suppl. A): 424, 1970.

11. Brittberg, M.; Lindahl, A.; Nilsson, A.; Ohlsson, A.; Isaksson, O.; and Peterson, L.: Treatment of deep cartilage defects in the knee with autologous chondrocyte transplantation. *New England J. Med. Res.* 331: 889, 1994.
12. Vacanti, C. A.; Kim, W.; Schloo, B.; Upton, .l.; and Vancanti, J. P.: Joint resurfacing with cartilage grown in situ from cellpolymer structures. *Amer. d. SportsMed.* 22: 485, 1994.
13. Ma, P. X.; Schloo, B.; Mooney, D.; and Langer, R.: Development of biomechanical properties and morphogenesis of in vitro tissue engineered cartilage. *J. Biomed Mater. Res.* 29:1587,1995.
14. Chu, C. R.; Coutts, R. D.; Yoshioka, M.; Harwood, F. L.; Monosov, A. Z.; and Amiel, D.: Articular cartilage repair using allogenic perichondrocyte seeded biodegradable porous polylactic acid (PLA): A tissue-engineering study. *J. Biomed Mater. Res.* 29:1147, 1995.
15. Grande, D. A.; Halberstadt, C.; Naughton, G.; Schwartz, R.; and Manji, R.: Evaluation of matrix scaffolds for tissue engineering of articular cartilage grafts. *J. Biotaed Mater. Res.* 34:211, 1997.

What is claimed is:

1. A surgical procedure wherein chondrocytes are taken from a patient and rapidly multiplied and transplanted into said patient for cartilage repair, comprising the steps of:
   1) obtaining cartilage tissue from knee cartilage, nasal septal cartilage, ear cartilage or costo-chondral cartilage of a patient,
   2) treating said cartilage to obtain chondrocytes therefrom,
   3) culturing the chondrocytes to obtain an adequate sample of chondrocytes,
   4) plating and growing the chondrocytes onto a scaffold, and
   5) surgically implanting the chondrocyte bearing scaffold into said patient, wherein the entire surgical procedure is carried out expeditiously with good quality chondrocytes being returned to the patient and the scaffold being reabsorbed leaving in place viable chondrocytes, wherein the scaffold is prepared by crosslinking a polysaccharide with a polyamine, thereby forming a crosslinked polysaccharide derivative.

2. The surgical procedure of claim 1 wherein the cartilage obtained is nasal septal cartilage.

3. The surgical procedure of claim 1 wherein the polysaccharide is selected from the group consisting of arabinogalactan and oxidized arabinogalactan, and the polyamine is selected from the group consisting of glutamic acid, albumin, gelatin and lysine.

4. The surgical procedure of claim 1 wherein the polysaccharide is selected from the group consisting of dextran, cellulose, arabinogalactan, pollulan and amylose.

5. The surgical procedure of claim 1 wherein the polysaccharide used to prepare the crosslinked polysaccharide derivative is a member selected from the group consisting of dextran, arabinogalactan, pollulan, cellulose and amylose; with the polysaccharide derivative being crosslinked by a polyamine compound selected from the group consisting of lysine, ethylenediamine, alkylenediamine, phenylenediamine, xylenediamine, polyethylenimine, gelatin, albumin, fibrinogen and

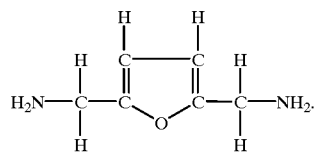

6. The surgical procedure of claim 1 wherein the scaffold used for cartilage repair comprises a polysaccharide selected from the group consisting of dextran, arabinogalactan, pollulan, cellulose and amylose crosslinked by a polyamine compound selected from the group consisting of lysine, ethylenediamine, alkylenediamine, phenylenediamine, xylenediamine, polyethylenimine, gelatin, albumin, fibrinogen and

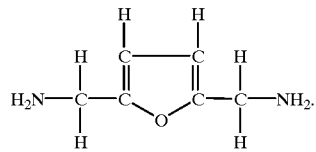

7. The surgical procedure of claim 1 wherein the scaffold growing chondrocytes thereon is surgically implanted into the knee, head or neck area.

* * * * *

UNITED STATES PATENT AND TRADEMARK OFFICE
CERTIFICATE OF CORRECTION

PATENT NO. : 6,378,527 B1
DATED : April 30, 2002
INVENTOR(S) : Hungerford et al.

It is certified that error appears in the above-identified patent and that said Letters Patent is hereby corrected as shown below:

<u>Title page,</u>
Item [73], change to read:
-- [73] Assignees: The Johns Hopkins University, Baltimore; Chondros, Inc., Towson; both of MD (US). --

<u>Column 6,</u>
Line 12, "chondroctyes" should read -- chondrocytes --.

Signed and Sealed this

Eighth Day of October, 2002

Attest:

Attesting Officer

JAMES E. ROGAN
*Director of the United States Patent and Trademark Office*